US012447280B2

(12) United States Patent
Urbanek et al.

(10) Patent No.: US 12,447,280 B2
(45) Date of Patent: Oct. 21, 2025

(54) CONNECTION MECHANISM FOR AN AUXILIARY MODULE

(71) Applicant: Ypsomed AG, Burgdorf (CH)

(72) Inventors: Leos Urbanek, Bern (CH); Jürg Hirschel, Bern (CH); Marcel Allenspach, Burgdorf (CH); Gabriel Kalbermatter, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 1154 days.

(21) Appl. No.: 16/994,151

(22) Filed: Aug. 14, 2020

(65) Prior Publication Data

US 2020/0376203 A1 Dec. 3, 2020

Related U.S. Application Data

(63) Continuation of application No. PCT/IB2019/050927, filed on Feb. 6, 2019.

(30) Foreign Application Priority Data

Feb. 15, 2018 (CH) .................................... 00183/18

(51) Int. Cl.
*A61M 5/315* (2006.01)
*A61M 5/32* (2006.01)

(52) U.S. Cl.
CPC ...... *A61M 5/31566* (2013.01); *A61M 5/3156* (2013.01); *A61M 5/3158* (2013.01); *A61M 5/3202* (2013.01); *A61M 2205/50* (2013.01)

(58) Field of Classification Search
CPC .......... A61M 5/31566; A61M 5/31565; A61M 5/315; A61M 5/31; A61M 5/178;
(Continued)

(56) References Cited

U.S. PATENT DOCUMENTS 8,652,100 B1 2/2014 Cowe
10,283,014 B2 5/2019 Baker et al.
(Continued)

FOREIGN PATENT DOCUMENTS

CH 713129 A2 5/2018
EP 2781230 A1 9/2014
(Continued)

OTHER PUBLICATIONS

International Preliminary Report on Patentability received for International Application No. PCT/IB2019/050927 mailed on Aug. 18, 2020, 9 pages.
(Continued)

*Primary Examiner* — Kevin C Sirmons
*Assistant Examiner* — Alexandra Lalonde
(74) *Attorney, Agent, or Firm* — Dorsey & Whitney LLP

(57) ABSTRACT

An auxiliary module for connecting to an injector for dispensing a medical substance comprises a housing having a retaining device, and a receiving unit having a retaining element, wherein the receiving unit is movable relative to the housing. The auxiliary module includes a retaining configuration, in which the receiving unit is immovably retained in the housing by the retaining device, and in which the retaining element can cooperate with the injector in such a way that the injector is retained by the receiving unit and the retaining element is locked by the housing. The auxiliary module also includes a release configuration, in which the receiving unit is released from the retaining device and the injector is released from the retaining element. The auxiliary module can be adjusted from the retaining configuration into the release configuration, and back again, by an adjustment movement of the receiving unit.

17 Claims, 9 Drawing Sheets

(58) Field of Classification Search

CPC ............ A61M 5/3156; A61M 5/31548; A61M 5/31545; A61M 5/3158; A61M 5/20; A61M 5/24; A61M 2205/50; A61M 2005/3126; A61M 5/3202; A61M 5/14546; A61M 5/1458; A61M 5/3135; A61M 2005/14268; A61M 2005/14553; A61M 2005/2006; A61M 2005/2433; A61M 2005/244; A61M 2005/2451; A61M 2005/2485; A61M 2005/2492; A61M 2005/3142; A61M 2005/3143

See application file for complete search history.

(56) References Cited

U.S. PATENT DOCUMENTS

| | | | | |
|---|---|---|---|---|
| 10,795,973 | B2 | 10/2020 | Baker et al. | |
| 2011/0004165 | A1* | 1/2011 | Iio | A61M 5/24 604/197 |
| 2011/0224616 | A1 | 9/2011 | Slate et al. | |
| 2013/0079718 | A1 | 3/2013 | Shang et al. | |
| 2013/0281936 | A1 | 10/2013 | Kemp et al. | |
| 2014/0194826 | A1 | 7/2014 | Nielsen et al. | |
| 2015/0025470 | A1 | 1/2015 | Baran et al. | |
| 2016/0022922 | A1 | 1/2016 | Kemp et al. | |
| 2016/0193414 | A1 | 7/2016 | Mcloughlin et al. | |
| 2016/0354556 | A1 | 12/2016 | Zucker et al. | |
| 2017/0000950 | A1* | 1/2017 | Baran | A61M 5/31525 |
| 2017/0000955 | A1 | 1/2017 | Mcloughlin et al. | |
| 2017/0259002 | A1 | 9/2017 | Laiosa et al. | |
| 2018/0236185 | A1* | 8/2018 | Säll | A61M 5/20 |
| 2019/0060579 | A1 | 2/2019 | Daniel | |
| 2020/0114082 | A1 | 4/2020 | Melander et al. | |
| 2021/0187200 | A1 | 6/2021 | Urbanek et al. | |

FOREIGN PATENT DOCUMENTS

| | | | |
|---|---|---|---|
| EP | 3626288 | A1 | 3/2020 |
| WO | 03011370 | A2 | 2/2003 |
| WO | 2009152542 | A1 | 12/2009 |
| WO | 2010037828 | A1 | 4/2010 |
| WO | 2010098927 | A1 | 9/2010 |
| WO | 2010128493 | A2 | 11/2010 |
| WO | 2013004843 | A1 | 1/2013 |
| WO | 2013120774 | A1 | 8/2013 |
| WO | 2013120775 | A1 | 8/2013 |
| WO | 2013153121 | A2 | 10/2013 |
| WO | 2018064784 | A1 | 4/2018 |
| WO | 2019159035 | A1 | 8/2019 |
| WO | 2020058875 | A1 | 3/2020 |

OTHER PUBLICATIONS

International Preliminary Report on Patentability received for International Application No. PCT/IB2019/057866, mailed on Mar. 23, 2021, 9 pages.

* cited by examiner

CONNECTION MECHANISM FOR AN AUXILIARY MODULE

RELATED APPLICATIONS

This application claims priority to International Application No. PCT/IB2019/050927 filed on Feb. 6, 2019, entitled "CONNECTION MECHANISM FOR AN AUXILIARY MODULE", which in turn claims priority to Swiss Application No. 00183/18 filed Feb. 15, 2018, each of which is incorporated by reference herein, in the entirety and for all purposes.

TECHNICAL FIELD

The present invention relates to the field of medical injection devices for administering liquid substances, in particular drugs or medical substances such as insulin and hormone preparations. The invention relates to a connection mechanism of an auxiliary module for a detachable connection of the auxiliary module to an injection device.

BACKGROUND OF THE INVENTION

From the prior art, auxiliary modules are known which can be detachably connected to an injector. Such auxiliary modules are reusable and can be connected to a disposable injector such as, for example, an autoinjector, or to a reusable injector. The auxiliary modules are also referred to as electronics module, "smart device," "smart module" or "add-on." The auxiliary modules may perform sensing, computing and/or communications relating to the injectors, e.g., are used to detect processes, events and functions of the disposable injector, and to monitor and/or report detected events to the user. Thus, for example, during the injection process, the user can be assisted in real time by the auxiliary module, in that, in an application on a smartphone, instructions for the injection, suggestions for the injection time and handling errors are displayed. Furthermore, by means of the auxiliary module, visual and acoustic feedback for specific events such as, for example, the successful completion of an injection, can be output. The auxiliary module can also record information on injections that have been performed and transfer the information or perform evaluations using the recorded data.

Before the start of the injection, the auxiliary module is connected to an injector, in that this module is detachably put or plugged onto the disposable injector. For this connection of the auxiliary module to the injector, various connection mechanisms are known.

For example, patent application US 2015/0025470 A1 describes such a detachable connection between an auxiliary module and an injector. In order to connect the injector to the auxiliary module, the injector is introduced into an opening of the auxiliary module. If the injector is correctly oriented with respect to the auxiliary module, a rib attached to an outer surface of the injector is received in a groove in the auxiliary module and the injector can be introduced completely into the auxiliary module. In order to fasten the auxiliary module on the injector, the user rotates a securing ring which surrounds securing arms oriented in the longitudinal direction and is in threaded connection with said securing arms. Due to the rotation, the securing ring is moved in the longitudinal direction and relative to the injector, whereby the free ends of the securing arms are pressed radially inward onto the outer surface of the injector. The auxiliary module is held thereby on the injector.

This connection has the disadvantage that the user must carry out multiple steps, namely the sliding on and the subsequent tightly screwing on with the securing ring, in order to be able to securely connect the auxiliary module to the injector.

The patent application WO 2013/120775 A1 describes an additional connection mechanism for fastening an auxiliary module on an injector. For the connection, the injector is introduced into an opening in the auxiliary module. Here, the auxiliary module must be set at an angle with respect to the injector, so that the longitudinal axis of the auxiliary module forms an acute angle with respect to the longitudinal axis of the injector. Subsequently, the auxiliary module is pivoted toward the injector, so that the two longitudinal axes are arranged parallel to one another. During the pivoting, two lateral wings of the auxiliary module are pressed apart. If the auxiliary module can be pivoted down completely onto the injector, the wings again move slightly toward one another. Here, a respective projection at the respective end of the wings engages in a lateral recess in the injector. Since the wings are pretensioned toward one another and thus press from both sides against the injector, the projections of the wings are clipped or snapped into the recesses.

In this connection as well, the user cannot connect the injector to the auxiliary module in one step, but instead must perform several steps. In addition, a securing or locking of the connection is lacking.

WO 2003/011370 A2 discloses a connection mechanism comprising a clip-on device which engages in a groove in the injector. Here, the clip-on device is additionally pressed by means of a compression spring against the injector. At the beginning and during the dispensing, a locking slide, which is coupled to the drive device, secures the clip-on device, so that the latter cannot be released from the groove. At the end of a dispensing, the locking slide releases the clip-on device. The injector can be released from the auxiliary module.

In this connection mechanism, for the connection of the injector to the auxiliary module, the user must keep the release button pressed during the introduction of the injector and at the same time position the injector in the direction of rotation. This makes the handling difficult for the user.

DESCRIPTION OF THE INVENTION

One aim of the invention is to enable a simple and reliable connection of the auxiliary module and the injector. This aim is achieved by an auxiliary module and a method for connecting an injector to or with an auxiliary module according to the claims. Certain embodiments or features are the subject matter of dependent claims.

According to the invention, the auxiliary module comprises a housing with a retaining device and a receiving unit with a retaining element, wherein the receiving unit can be moved relative to the housing and wherein a. the auxiliary module has a retaining configuration, in which the receiving unit is retained in the housing by the retaining device or retainer and in which the retaining element can cooperate with the injector in such a way that the injector is retained by the receiving unit;
b. the auxiliary module has a release configuration, in which the receiving unit is released from the retaining device or retainer and the injector is released from the retaining element.

Here, the auxiliary module can be adjusted by an adjustment movement of the receiving unit from the retaining configuration into the release configuration and back again.

Since, by a simple adjustment movement of the receiving unit, the auxiliary module can be adjusted from the retaining configuration, in which the injector is retained in the housing of the auxiliary module, into the release configuration, in which the injector is released from the retaining element, and back again, the connection of the injector to the auxiliary module and the release of the injector from the auxiliary module are facilitated. This means that, by means of a single movement of the receiving unit, which can be generated, for example, by inserting the injector into the housing, the user can adjust the auxiliary module into the retaining configuration and thereby connect the injector to the auxiliary module in a simple manner.

Here, without additional process steps of the user, at the end of the adjustment movement, the receiving unit is retained in the housing by the retaining device. In addition, by means of the single adjustment movement, the retaining element is adjusted, so that it can retain the injector.

Equally simply, the injector can be released again from the auxiliary module. After the release of the receiving unit from the retaining device or retainer, by means of a single adjustment movement of the receiving unit, the auxiliary module can be adjusted from its retaining configuration into its release configuration. During this single adjustment movement, the retaining element is separated from the injector, so that the retaining element can be pulled back, and as a result it can release the injector from the receiving unit. Here, for example, by means of an elastic element, a portion of the mechanism can be automated, so that, for example, the user only needs to release the receiving unit from the retaining device, and the adjustment movement is automatically triggered by the release.

In addition, by means of the connection according to the invention, the injector is securely connected to the auxiliary module, and the auxiliary module cannot be accidentally released from the injector. Thus, for example, the auxiliary module remains securely connected to the injector even if the user pulls off a closure or cap in the distal, puncture-side region of the injector and holds the injector above the auxiliary module in the proximal region.

In the present description, the term "injector" is understood to mean a device in which the injection needle or cannula is removed from the tissue of the patient, immediately or after a retaining time of short duration, e.g., less than 1 minute after the dispensing of the medical substance. Thus, in the case of an injector, in contrast to an infusion system, the injection needle or the cannula does not remain permanently or for a longer time period of several hours in the patient.

The injector can be a disposable injector or a reusable injector. A disposable injector is an injector which is used to subcutaneously inject a medical substance located in a non-refillable or non-exchangeable carpule or prefilled syringe. If the quantity of the medical substance provided for the injection has been injected in one injection step or multiple injection steps, the disposable injector is disposed of. The carpule or prefilled syringe cannot be exchanged in the disposable injector. In contrast, in a reusable injector, the carpule or prefilled syringe with the medical substance is exchangeable.

The injector preferably has an elongate shape which defines a longitudinal axis. In the present description, the terms "axial" and "longitudinal axis" are both used to refer to a direction parallel to this longitudinal axis of the injector. Moreover, the term "distal" refers to a direction toward the puncture-side end of the injector. The term "proximal," on the other hand, relates to a direction toward the rear end of the injector, which faces or is opposite to the puncture-side end.

In this connection, the term "drug" or "medical substance" comprises any flowable medical formulation, which is suitable for the controlled administration by means of a cannula or hollow needle, of, for example, a fluid, a solution, a gel or a fine suspension containing one or more medical active ingredients. Thus, a drug can be a composition with a single active ingredient or a premixed or co-formulated composition with several active ingredients from a single container. The term in particular includes drugs such as peptides (for example, insulins, insulin-containing drugs, GLP-1-containing as well as derived or analogous preparations), proteins and hormones, biologically obtained or active substances, active substances based on hormones or gels, nutrition formulations, enzymes and additional substances both in solid (suspended) or in liquid form. The term moreover also comprises polysaccharides, vaccines, DNA or RNA or oligonucleotides, antibodies or parts of antibodies as well as suitable base, auxiliary and carrier substances.

The receiving unit comprises at least one retaining element for retaining the injector on or in the receiving unit. In the retaining configuration, the retaining element preferably engages in a recess in the injector in order to retain the injector. In a one embodiment, the receiving unit comprises at least two retaining elements, so that the injector can be retained reliably. For the sake of simplicity, only a single retaining element is used in the following description. If the receiving unit comprises multiple retaining elements, the mentioned features relate to all the retaining elements of the receiving unit.

The retaining element may be formed as a retaining arm which can be moved relative to the receiving unit. However, in alternative embodiments, the retaining element can also be formed as a hook, for example.

In the retaining configuration, the retaining element cannot or may not be moved except for a slight play. Thereby, in the retaining configuration, the injector is securely retained on or by the receiving unit.

The receiving unit is used to retain the injector in the housing of the auxiliary module in the retaining configuration. The receiving unit itself is retained by means of the retaining device or retainer in the retaining configuration in the housing of the auxiliary module. Thus, the injector is, in one embodiment, not held directly by the housing but via the receiving unit in the housing of the auxiliary module. Preferably, the receiving unit is formed in the shape of a sleeve, and the injector can be introduced into the sleeve shape of the receiving unit. However, the receiving unit may also have a different shape. For example, it may be designed as a half shell or as a container. In addition, the receiving unit may also be formed, for example, as a plate with a circumferential wall, which forms a cavity, in which the injector may be received. Independently of the shape of the receiving unit, said receiving unit can be moved relative to the housing. The receiving unit may be guided in a manner so it can be displaced on or in the housing. However, alternatively, the receiving unit may also be mounted in such a manner that it can be rotated or displaced and rotated on or in the housing.

The housing preferably has an opening in which the receiving unit is located. However, this shape of the housing is not absolutely necessary. For example, the housing can also be in the shape of a half shell or it can be designed as a rectangular or cylindrical body with an opening on one side. Furthermore, the housing can be designed as a hollow body with a continuous opening.

In the retaining configuration, the retaining device or retainer retains the receiving unit in the housing, so that the receiving unit cannot be freely moved relative to the housing. The receiving unit may be held by the retaining device in such a manner that it cannot be moved relative to the housing except for a slight mechanical play. In the release configuration, on the other hand, the receiving unit is released from the retaining device. The receiving unit may then be still mounted on the housing, so that it cannot be released from the housing; however, it can be freely moved relative to the housing. Hooks, cams or protrusions of the retaining device or retainer may used for retaining the receiving unit on or in the housing. Advantageously, a cam may engage in or with a correspondingly shaped counter-element in the receiving unit, in order to retain the receiving unit in the housing, in the retaining configuration.

The auxiliary module can assume the retaining configuration or the release configuration. Advantageously, the auxiliary module may be adjusted or transferred by means of a single adjustment movement of the receiving unit from the retaining configuration into the release configuration or from the release configuration into the retaining configuration. In the retaining configuration, the injector is immovably retained by means of a retaining element on or of the receiving unit, which in turn is retained by means of the retaining device or retainer in the housing of the auxiliary module. The injector may be connected via the receiving unit to the auxiliary module in such a manner that the auxiliary module can by means of sensors detect changes or movements of the injector, in particular injection events in the injector. In contrast, in the release configuration, the injector is not retained in the receiving unit and thus not connected to the auxiliary module. This means, in the release configuration, the injector is separate or separable from the auxiliary module, and the auxiliary module cannot detect changes or movements of the injector, in particular injection events in the injector. In the release configuration, the injector can be removed from the auxiliary module.

In the retaining configuration, the retaining element may be locked by the housing. Thus, the injector is retained not only in the housing of the auxiliary module, but also additionally secured against accidental release by locking. The term "locked" means that the retaining element cannot be moved out of a position in which it can retain the injector. The retaining element is thus prevented from moving in a release direction as a result of the locking. In order to separate the injector from the auxiliary module, the locking of the retaining element accordingly must be released, and the retaining element must be moved away by the injector.

If the retaining element is not locked by the housing, the retaining element can still retain the injector in the housing, but the retaining element cannot be moved out of the retaining position without difficulty. For the locking of the retaining element, the housing interacts directly or indirectly via an intermediate element which belongs to the housing with the retaining element. Preferably, the housing or an intermediate element belonging to the housing surrounds the retaining element at least partially, in order to lock the retaining element. Preferably, at the end of the adjustment movement, the retaining element is locked by the housing.

In a preferred embodiment, the receiving unit can be displaced by a linear displacement movement for the adjustment or the transfer of the auxiliary module from the retaining configuration into the release configuration and back again. This means that the adjustment movement is not a rotation or screw movement but a linear movement for the linear displacement of the receiving unit relative to the housing. This offers the advantage that the receiving unit can be adjusted particularly quickly, and as a result the auxiliary module can be adjusted correspondingly quickly from the retaining configuration into the release configuration or from the release configuration into the retaining configuration. The linear adjustment movement may occur parallel to the longitudinal axis of the housing. Thereby, the adjustment movement may be generated by a relative movement between the injector and the auxiliary module, for example, by inserting the injector into the auxiliary module.

In an alternative embodiment, the adjustment movement of the receiving unit may be, for example, a rotation or screw or curvilinear movement.

Preferably, the housing is designed in the shape of a sleeve and surrounds the injector introduced into the housing. In the process, the sleeve-shaped housing preferably guides the injector in an insertion direction. Here, it is not absolutely necessary that the housing surround the injector on all sides in the retaining configuration. In one embodiment, the housing surrounds the injector only with regard to its lateral surfaces. This means that, in the retaining configuration, at least one front surface of the injector is not surrounded by the housing. In addition, in one embodiment, the housing surrounds the injector with respect to the length of the injector only partially. Advantageously, the receiving unit, in particular the sleeve-shaped receiving unit, may be received in the sleeve shape of the auxiliary device housing.

Advantageously, the receiving unit may comprise an axial abutment element for the injector. This enables a simple and quick positioning of the injector relative to the receiving unit in the axial direction of the housing. This is particularly important if the retaining element has to interact at a certain site on the injector, for example, with a recess, in order to retain the injector. In addition, the positioning of the injector relative to the housing is important, if the injector and the housing each comprise contacts or engagement surfaces which have to be aligned with respect to one another in the retaining configuration.

In one embodiment, the abutment element may comprise an abutment surface that is oriented perpendicular to the longitudinal axis of the housing and against which a front side of the injector abuts, if the injector is introduced into the housing of the auxiliary module. Advantageously, the abutment surface together with the receiving unit may be moved relative to the housing. In this case, the receiving unit may be moved by means of the abutment element. Alternatively, the possibility also exists that the receiving unit does not comprise an abutment element. In this case, the injector must be positioned by means of a marking relative to the housing, and the receiving unit must be displaced manually relative to the housing.

In one embodiment, the receiving unit may be pretensioned by an elastic element in the direction of a longitudinal axis of the housing in the retaining configuration. In one embodiment, the elastic element may be tensioned during the adjustment of the auxiliary module from the release configuration into the retaining configuration and relaxed during the adjustment from the retaining configuration into the release configuration. Thus, for example, by releasing or reducing the pretension, the adjustment movement of the receiving unit can be generated, whereby the auxiliary module can be adjusted from its retaining configuration into its release configuration. For example, the elastic element can be designed as a mechanical spring or as an elastic or resilient plastic element.

In a one embodiment, the retaining element can be moved for retaining the injector substantially in a direction perpendicular to the longitudinal axis of the auxiliary module and it comprises a projection for interaction with the injector. If the retaining element is moved in this direction toward the inserted injector, it reaches a retaining position, engages in the injector and holds said injector in the receiving unit. If the retaining element is moved away from the injector, the injector is released from the retaining element. The retaining element here may be connected to the receiving unit. This means that the retaining element is not guided by the receiving unit but may be connected to said receiving unit via an articulation in such a manner that it can be moved.

The projection can be in the form of a nose, a cam, a half sphere or hook, wherein the projection can engage in a correspondingly shaped recess, indentation, deepening or groove in the injector. If the retaining element is formed as a retaining arm, the projection may be located in a region of a free end of the retaining arm.

The retaining element is retained in a manner so it may be pivoted and in particular elastically pivoted on the receiving unit. By the pivoting movement, the retaining element can be pivoted simply and quickly toward the inserted injector, in order to retain said injector. If the retaining element is additionally elastically pivotable, it can be pretensioned against the injector. If the injector is introduced into the housing, in this case the retaining element snaps with the projection into a recess in the injector and thereby reliably retains the injector. Thus, a simple connection of the injector to the auxiliary module is made possible.

In the region of a free end of the retaining element, the retaining element may comprise a protrusion for engaging into the housing by and upon forced release of the cam or other projection from the injector. The free end of the retaining element here is the end which is not connected to the receiving unit or retained or guided by the receiving unit. However, in an alternative embodiment, the possibility also exists that the protrusion is arranged between the ends or in the middle of the retaining element.

In one embodiment, the protrusion may be guided through the housing in such a manner that the projection at the same time is pulled back from the injector inserted in the housing, if the retaining element is moved away from the inserted injector. Moreover, preferably, the protrusion is moved out of the housing wall in the direction of the middle of the housing, and at the same time the projection engages in the injector inserted in the housing, if the retaining element is moved toward the inserted injector. Thus, the protrusion is used to move the retaining element in a guided manner away from the injector or in a guided manner toward the injector.

The engagement of the protrusion in the housing is particularly advantageous if the retaining element is elastically pretensioned toward the injector inserted in the housing. In this case, the retaining element in fact must be moved away from the injector for the release from the injector against the pretensioning force. This can be achieved in that the protrusion is introduced into the housing, and thereby the retaining element is moved in a guided manner away from the inserted injector by the injector.

In one embodiment, the retaining element is designed as an elongate retaining arm, wherein the protrusion is located on a first side of the free end of the retaining arm and the projection is located on a second side of the free end of the retaining arm, which faces the first side.

In an alternative embodiment, the first side of the free end of the retaining arm comprises no protrusion. Instead, a respective protrusion is located on the side surfaces of the retaining arm, and the projection is located on the second side of the free end of the retaining arm. The protrusions thus protrude laterally in a direction perpendicular to the first and second sides. This embodiment offers the advantage that the retaining arm needs less space in the radial direction. Correspondingly, the auxiliary module can be constructed compactly.

In both variants, by a pivot movement of the retaining arm, either the protrusion or the protrusions can engage in the housing or the projection can be displaced toward the inserted injector, so that the projection can interact with the injector. The retaining arm thus makes it possible that the protrusion can be adjusted simply and quickly. In a preferred embodiment, the retaining arm is elastically pretensioned toward the middle longitudinal axis of the receiving unit or toward the inserted injector.

In addition, in one embodiment, the receiving unit comprises at least two retaining arms, which are arranged so that they face one another. The injector can thereby be held particularly securely in the housing.

Advantageously, in the retaining configuration, the retaining element may be located in a retaining position, in which the protrusion or a portion of the retaining element is locked by the housing, so that the retaining element cannot be moved relative to the receiving unit, and in which the projection engages in the injector inserted in the housing. This means that the housing locks the protrusion, so that the retaining element cannot be moved by means of the release movement out of its retaining position away from the inserted injector. The injector is thus retained securely in the retaining configuration in the housing of the auxiliary module and secured against unintended or spontaneous release.

The locking of the retaining element by the housing may occur in that the housing or an element belonging to the housing contacts the protrusion with a surface, whereby the retaining element is prevented from moving from a middle or internal space of the receiving unit outward or away from the inserted injector. Although, in the retaining position, the retaining element is locked in a manner so it cannot move, this does not rule out that the retaining element can move as a result of a slight play in a region, preferably in a region which is smaller than one millimeter. This play, which may be present, ensures that the retaining element is not blocked or jammed undesirably in the housing.

In another embodiment, the locking of the retaining element can occur, for example, in that the protrusion is retained in a guide in the housing, whereby the retaining element cannot move away from the injector.

Alternatively, the possibility exists that the retaining element is not locked in the retaining configuration but only retained. Correspondingly, in this case, the retaining element is not secured against accidental or spontaneous release.

Preferably, in the release configuration, the retaining element is in a release position, in which the protrusion is received in a recess in the housing and in which the projection is pulled back from an internal space of the receiving unit, so that the injector is released from the projection. In the release position, the protrusion may be received in a guide in the housing, so that it cannot be accidentally released from the housing.

In the release position, the projection may be moved from the internal space of the receiving unit. This means that, if the injector is introduced into the housing, it does not come in contact with the projection of the retaining element. This has the advantage that the injector can be inserted without resistance into the housing.

The movement of the retaining element may be coupled to the movement of the receiving unit. In this case, in one embodiment, due to the adjustment movement of the receiving unit in a first direction, in order to adjust the auxiliary module from the retaining configuration into the release configuration, the retaining element is guided from its retaining position into its release position. As a result of this single adjustment movement of the receiving unit, the projection is preferably pulled back out of its recess in the injector, and the protrusion is introduced into a recess in the housing.

In addition, by means of the adjustment movement of the receiving unit into a second direction, in order to adjust the auxiliary module from the release configuration into the retaining configuration, the retaining element is moved from its release position into its retaining position. By means of this single adjustment movement of the receiving unit, in one embodiment the protrusion may be released from the housing and the projection of the retaining element may engage with the injector inserted in the housing, whereby the injector is immovably retained on the receiving unit.

In one embodiment, the second direction is opposite the first direction. Since it is possible, by means of a single adjustment movement, to adjust the auxiliary module from the retaining configuration into the release configuration and back again, the connection of the injector to the auxiliary module and the release of the injector from the auxiliary module is simplified for the user.

In one embodiment, the auxiliary module may only be adjusted into the retaining configuration if the retaining element can be moved into its retaining position. For example, the retaining element cannot be moved into its retaining position, if the projection cannot be moved into the internal space of the receiving unit. This is the case, for example, if an injector is introduced into the housing but no recess for the projection is present, and thus the projection cannot interact with the injector. This case can occur in particular if the injector or at least the protrusion for the projection is not designed to be rotationally symmetric and if it is introduced in an incorrect rotational orientation into the housing.

The auxiliary module, which can only be adjusted into the retaining configuration if the retaining element can be moved into its retaining position, thus ensures that the injector cannot be connected to the auxiliary module in an incorrect rotational orientation, in which the auxiliary module cannot optimally detect the injection events in the injector. Such a mechanism can also be referred to as anti-twist device, since the injector can be retained only in a certain rotational orientation in the housing.

In an embodiment, the retaining device or retainer comprises a guiding cam and the receiving unit comprises a locking cam, wherein, in the retaining configuration, the guiding cam interacts in such a manner with the locking cam that the receiving unit is immovably retained in the housing by the elastic element, against a possible pretension in the direction of a longitudinal axis of the housing. This means that the receiving unit is immovably retained by the interaction of the locking cam with the guiding cam. Accordingly, the receiving unit cannot be moved without previous release of the locking cam from the guiding cam, in order to adjust by means of the adjustment movement the auxiliary module from the retaining configuration into the release configuration. By securing the interaction of the locking and guiding cams such as, for example, by a pretensioned spring, the receiving unit may be secured against accidental displacement, whereby the injector is secured against accidental release from the housing. The cams or their functions can also be interchanged; that is to say the movable guiding cam may also be arranged on the receiving unit.

In an embodiment, the guiding cam and the locking cam have a respective surface, the surfaces being in contact in such a manner that the locking cam is retained by the guiding cam.

Alternatively, the possibility also exists that the retaining device or retainer comprises no guiding cam and that the receiving unit comprises no locking cam. Thus, for example, the retaining device can comprise a pin and the receiving unit can comprise a slide control system, in which the pin of the retaining device is guided. Thus, the movements from one element of the retaining device or retainer onto the receiving unit or vice versa can be transferred by means of a slide control system.

In one embodiment, the guiding cam may be displaced along a securing path and adjusted from a retaining position, in which the guiding cam interacts with the locking cam, into a release position, in which the locking cam is released from the guiding cam. In an embodiment, in the retaining configuration, the guiding cam of the retaining device is in its retaining position. In the release configuration, on the other hand, the guiding cam can be in its release position, in its retaining position or in another position.

If the guiding cam is moved from its retaining position to a release position, it may be removed from the locking cam, whereby the receiving unit can freely move relative to the housing. Then, the auxiliary module may be adjusted by means of the adjustment movement of the receiving unit from the retaining configuration into the release configuration and back again.

The securing path may be linear. In one embodiment, the securing path is oriented perpendicular to the longitudinal axis of the housing. In alternative embodiments, the securing path may also be curved or be in the form of a helix. In this case, the guiding cam can be moved by a rotation or screw or curvilinear movement between its retaining position and its release position.

Preferably, the guiding cam can be pretensioned into its retaining position by a separate elastic securing element and thereby be secured against spontaneous release. As a result, the guiding cam must be moved against a pre-tensioning force, if it is moved along the securing path away from its retaining position, in order to enable an adjustment of the receiving unit and thus an adjustment of the auxiliary module from the retaining configuration into the release configuration. The elastic element may be a mechanical spring. Alternatively, the elastic element may also be formed, for example, by an elastic or resilient plastic.

In one embodiment, the guiding cam is in its retaining position both in the retaining configuration and in the release configuration. In this case, the pre-tensioning force of the elastic element must be overcome, if the receiving unit is adjusted into a first direction, in order to adjust the auxiliary module from the retaining configuration into the release configuration, as well as if the receiving unit is adjusted in the second direction, in order to adjust the auxiliary module from the release configuration into the retaining configuration.

By means of the pretension, it is ensured that the guiding cam cannot be accidentally released from its retaining position and thus accidentally release the locking cam of the receiving unit, whereby the receiving unit could adjust the auxiliary module from the retaining configuration into the release configuration. Thus, the pretension enables a secured retention of the injector in the housing of the auxiliary module.

Preferably, the retaining position is located on a first end of a securing path, the release position is located in a middle region of the securing path, and a released position is located on a second end of the securing path. This means that the guiding cam can be moved from its retaining position into its release position and from said release position into its released position and back again. The guiding cam may be in the release position, if the auxiliary module is in its release configuration.

Advantageously, the retaining device or retainer comprises a release button (which may be configured in a housing insert) by means of which the auxiliary module may be adjusted from its retaining configuration into its release configuration. Thereby, in a simple manner, the injector can be released from the housing of the auxiliary module. Preferably, during the actuation of the release button, the guiding cam of the retaining device or retainer is moved from its retaining position along the securing path toward its release position, whereby the locking cam of the receiving unit is released, and, as a result, the receiving unit can be moved relative to the housing.

Alternatively, the retaining device or retainer does not comprises a release button, and the receiving unit must be moved manually by the user in order to be able to adjust the auxiliary module from the retaining configuration into the release configuration.

In one embodiment, the retaining device with the release button as well as the retaining element is arranged in a distal region of the housing of the auxiliary module. Here, the distal region corresponds to a region of the housing, which faces the puncture-side region of the inserted injector. As a result, the retaining device with the release button and the retaining element are located in the region of an opening of the housing, and the proximal region of the housing remains free, so that the user can satisfactorily seize or grasp the auxiliary module in the proximal region.

This arrangement moreover has the advantage that the release button cannot easily be gripped by mistake by the user as a button for activating the dispensing, since usually such buttons for the dispensing are located in a proximal end region.

In addition, the invention relates to a method for connecting an injector to an auxiliary module, in particular to an auxiliary module as described above. The method comprises the steps a. introducing of the injector into the auxiliary module using an insertion movement;
b. adjusting, by the insertion, of a receiving unit in the housing of the auxiliary module relative to the housing;
c. moving, by the adjustment, of a retaining element toward the injector, so that the retaining element cooperates with the injector and thereby the injector is retained in the receiving unit;
d. securing of the receiving unit on the auxiliary module by a retaining device or retainer.

Preferably, the retaining element is locked by the housing, as a result of the adjustment of the receiving unit.

FIGURES

In connection with the appended figures, preferred embodiments of the invention are described below. They are intended to indicate basic possibilities of the invention and should in no case be interpreted in a limiting manner.

FIG. 1 shows a perspective view of an auxiliary module, which is connected to an injector;

FIG. 2 shows the individual parts of the auxiliary module;

FIG. 3 shows a cross-sectional view of the auxiliary module in the release configuration without inserted injector;

FIG. 4 shows a cross-sectional detail view of a middle region of the auxiliary module, in which region the retaining device or retainer can be seen in the release configuration;

FIG. 5 shows a cross-sectional view of the auxiliary module in the retaining configuration with inserted injector;

FIG. 6 shows a cross-sectional detail view of a middle region of the auxiliary module, in which region the retaining device or retainer can be seen in the retaining configuration;

FIG. 7 shows a cross-sectional view of the auxiliary module with an incorrectly inserted injector;

FIG. 8 shows a perspective view of an additional embodiment of the auxiliary module in the retaining configuration;

FIG. 9 shows a detail view of the additional embodiment from FIG. 8, wherein the upper half of the housing insert and of the release button is not represented;

FIG. 10 shows a perspective view of an embodiment of the auxiliary module in the retaining configuration with a concave housing shape;

FIG. 11 shows a side view from below of the embodiment from FIG. 10;

FIG. 12 shows a side view of the embodiment from FIGS. 10 and 11 in the release configuration, after injector removal.

The auxiliary module 2 is attached on the proximal end of the injector 1, wherein the proximal region of the injector 1 is retained in, and, in one embodiment, completely enclosed by, the auxiliary module 2. The distal region of the injector 1, on the other hand, is not surrounded by the auxiliary module 2.

Figure 1:
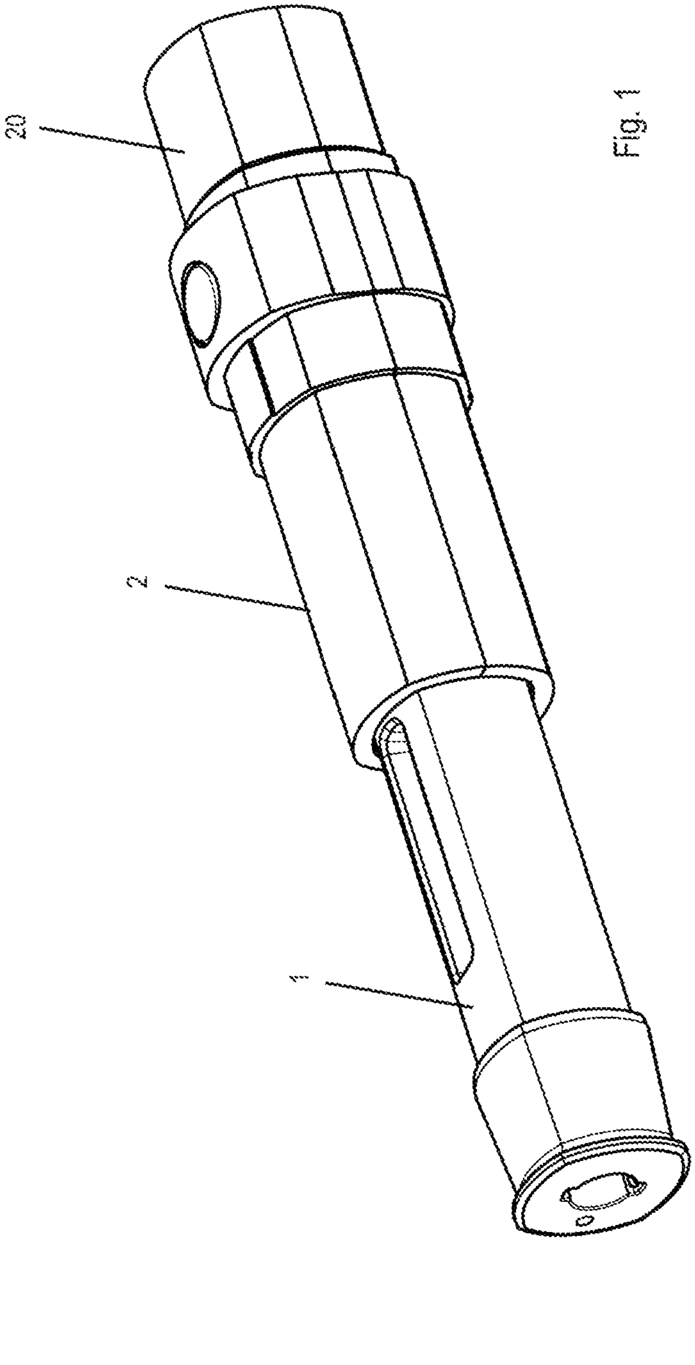
FIG. 1 shows, in a perspective view, an auxiliary module 2 according to the invention, which is connected to an injector 1, in the embodiment example shown, an autoinjector. In the present description, in the case of the auxiliary module 2, the end of the auxiliary module 2 that comprises the opening to an internal space is referred to as the distal end (in FIG. 1, left side) and the closed rear end of the auxiliary module 2 is designated as the proximal end (in FIG. 1, right side). In the case of the injector 1, the puncture-side end is referred to as the distal end and the rear end opposite the puncture-side end is referred to as the proximal end.
Figure 2:
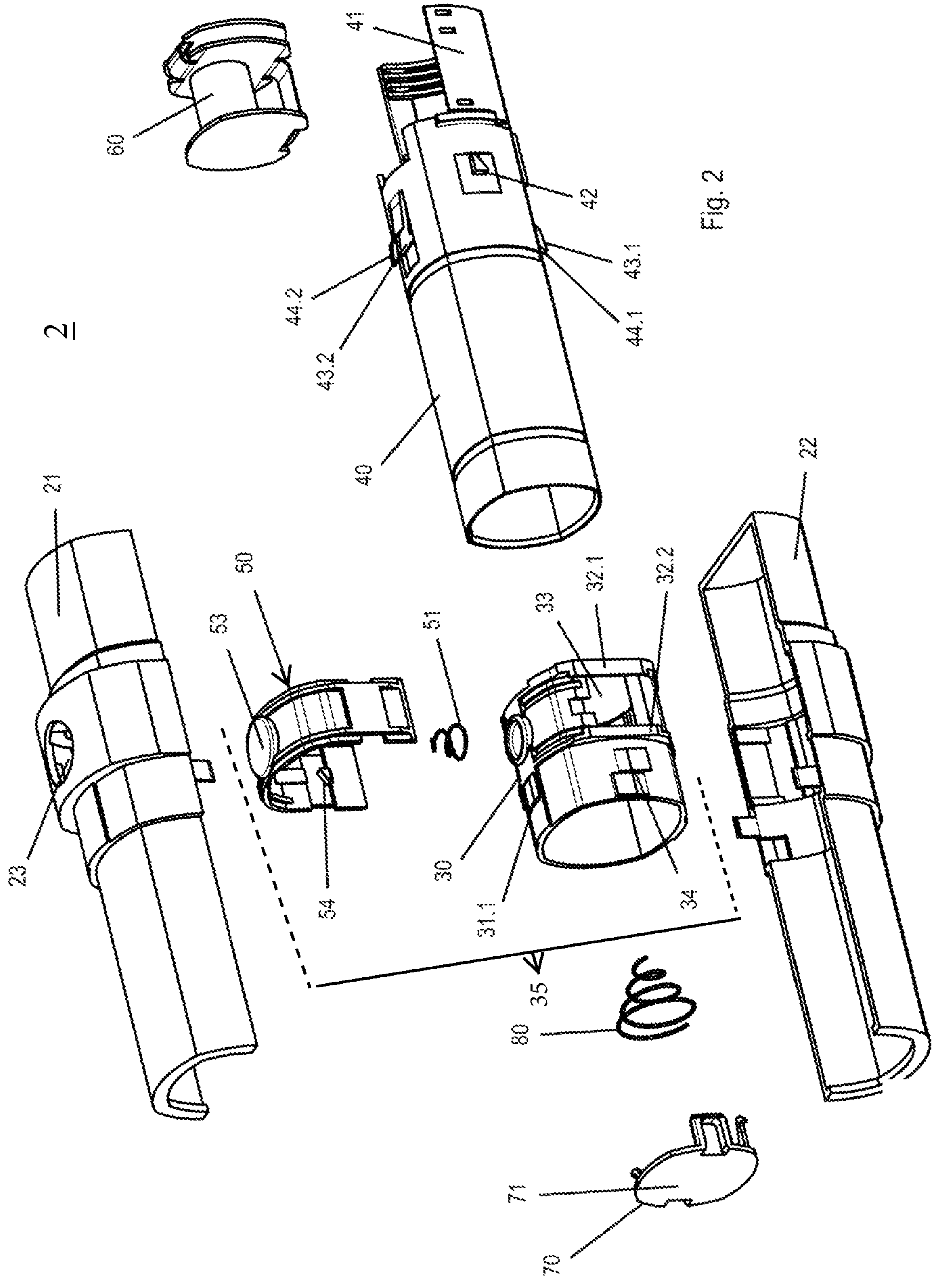

FIG. 2 represents the individual parts of the auxiliary module 2 according to the invention. Said individual parts are explained below. The auxiliary module 2 comprises a housing 20 formed by two parts, with an upper housing half 21 and a lower housing half 22, a housing insert 30 which belongs to the housing 20, a receiving unit 40 with an abutment element 70 and a compression spring 80, a release button 50 with a release button spring 51 and an electronics module 60.

The upper and the lower halves 21, 22 have a respective generally semi-circular shape and they are connected to one another by ultrasound welding. Alternatively, a connection by means of laser welding or gluing is also possible. Due to the semi-circular shape of the housing halves 21, 22, an internal space forms between them. On a proximal end of the housing halves 21, 22, said housing halves have a respective end wall, so that the internal space is delimited at the proximal end by this end wall. On the distal end, the housing halves 21, 22 are open. Thus, the housing 20 on the distal end has an opening to the internal space. In the internal space, the housing insert 30, the release button 50 and the receiving unit 40 are located. When viewed in the proximal direction, the electronics module 60 is accommodated behind the housing insert 30.

In a middle region of the semi-circular shape, the semi-circular upper housing half 21 has an opening 23, through which, in the mounted state, an actuation surface 53 of the release button 50 protrudes. On external ends, with respect to the cross section, the upper housing half 21 has a respective clip-on arm, arms which, during the connection to the lower housing half 22, clip into corresponding recesses in the lower housing half 22. In the same way, the semi-circular lower housing half 22 comprises clip-on arms which clip into recesses in the upper housing half 21, during the connection of the housing halves 21, 22. Due to this clip-on connection, the housing halves 21, 22 can be premounted before the ultrasound welding. The two housing halves 21, 22 form the housing 20 of the auxiliary module 2. In cross section, the housing 20 has an approximately square shape, wherein each side of the square is curved slightly outward.

In the following description, for the sake of simplicity, the direction from the middle longitudinal axis of the housing 20 outward toward the side walls of the housing 20 is referred to as the radial direction, in spite of the fact that the housing 20 in the embodiment shown does not have a purely circular cross section.

The housing insert 30 has a sleeve-shaped form. In two outer faces, the housing insert 30 has a respective opening 31.1, each of which extends inward in an acute angle with respect to the longitudinal axis of the housing insert 30 from an outer face in the proximal direction through the wall of the housing insert 30. The housing insert 30 moreover has, on two outer faces, a respective aperture 33 in the wall, through which guiding cams 54 of the release button 50 can interact with locking cams 42 of the receiving unit 40. Furthermore, the housing insert 30 mounts the release button 50 in a manner so that it can move. For this purpose, the housing insert 30 comprises, on two outer faces, two respective support surfaces 32.1, 32.2. The housing insert 30 is accommodated in a radial deepening in the housing 20, whereby the housing insert 30 is immovably secured to the housing 20. In the circumferential direction, the housing insert 30 is secured in such a manner that it cannot move relative to the housing 20 by two respective ribs 34 attached on two outer faces of the housing insert 30, which engage in corresponding grooves in the inner wall of the housing 20.

The release button 50 has a U-shaped cross section and is mounted on the housing insert 30, so that the limbs (or legs) of the U shape surround the housing insert 30 on both sides and rest on the support surfaces 32.1, 32.2. Between the limbs, on an outer face, the release button 50 comprises the actuation surface 53 which the user can actuate manually, in order to move the release button 50. Furthermore, the limbs comprise, on their inner face, a respective triangular guiding cam 54, each of which can interact with a triangular locking cam 42 of the receiving unit 40 and thereby form (with the housing insert 30) a retaining device or retainer for the receiving unit 40. The function of the guiding cams 54 is explained in detail below.

The release button 50 is located in the radial direction between housing insert 30 and housing 20. Here, the release button can move radially, in a direction perpendicular to the longitudinal axis of the housing 20, relative to the housing insert 30 and to the housing 20 along a linear securing path. Between the housing insert 30 and the release button 50 (which in this embodiment cooperate to form the retaining device or retainer 35), the release button spring 51 is located. Said release button spring pretensions the release button 50 radially outward In the internal space of the housing 20, the receiving unit 40 is located. Said receiving unit is movably mounted in the axial direction relative to the housing 20 and thus relative to the housing insert 30. The receiving unit 40 is also designed in the shape of a sleeve and it has substantially a square shape in cross section, wherein the side walls of the square are in each case curved slightly outward.

In an embodiment, the receiving unit 40 comprises, in its internal space, webs or ribs (not visible in FIG. 2) extending in the axial direction. As a result, an injector inserted into the internal space of the receiving unit 40 lies on the webs or ribs. Pressure-sensitive elements of the injectors such as, for example, electronic elements or NFC tags on the outer face of the injector can as a result be accommodated in the gaps between the webs or ribs. They are thus protected and not pressed onto the inner wall of the internal space of the receiving unit 40.

In a proximal region, the receiving unit 40 comprises a section 41 with a semi-circular shape in cross section. The electronics module 60 is accommodated in this section 41. Thus, the electronics module 60 with the receiving unit 40 can be moved relative to the housing.

On two mutually facing sides of the square shape of the receiving unit 40, a retaining element in the form of a retaining arm 43.1, 43.2 is arranged in each case, wherein the retaining arms 43.1, 43.2 are located, with respect to the axial length of the receiving unit 40, in a middle region of the receiving unit 40. The retaining arms 43.1, 43.2 are pivotably connected on a first end to the receiving unit 40. In the region of the free end on an outer face of the retaining arms 43.1, 43.2, which faces away from the internal space, said retaining arms have a respective protrusion 44.1, 44.2, each of which can be accommodated in the openings 31.1. On the protrusions 44.1, 44.2 a respective distal and a respective proximal sliding surface are formed. Said sliding surfaces are described in further detail below in connection with FIGS. 3 and 5. However, also in the region of the free end of the retaining arms 43.1, 43.2, on an inner face facing the internal space of the receiving unit 40, the retaining arms 43.1, 43.2 comprise a respective projection 45.1, 45.2. On the other two sides of the square shape, a triangular locking cam 42 is arranged in each case, each being capable of interacting with a guiding cam 54 of the release button 50.

Moreover, in its interior space, the receiving unit 40 comprises the abutment element 70 (FIG. 3) with an abutment surface 71 oriented perpendicular to the longitudinal axis of the receiving unit 40 and extending over the entire cross section of the internal space of the receiving unit 40. Here, the abutment element 70 is positioned in a proximal region of the receiving unit 40. In addition, the abutment element 70 is connected in such a manner that it cannot be moved, by means of a snap-on connection to the receiving unit 40.

Between the abutment element 70 and a wall of the housing oriented perpendicular to the longitudinal axis of the housing, which protrudes into the internal space of the housing, the compression spring 80 is located. Via the abutment element 70, this compression spring 80 pretensions the receiving unit 40 in the distal direction.

Figure 3:
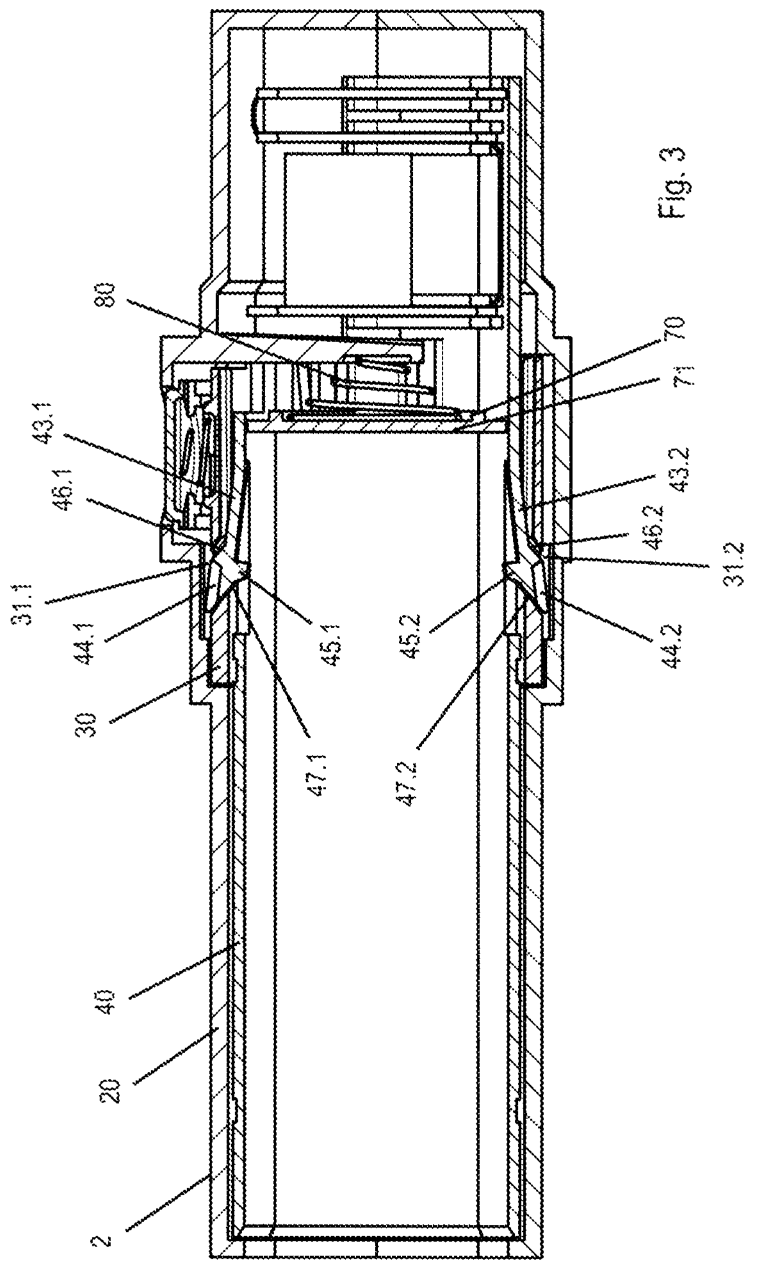

Release Configuration of the Auxiliary Module (FIG. 3, 4)

Below, the function of the auxiliary module 2 is discussed in detail. In FIG. 3, a cross-sectional view of the auxiliary module 2 in a release configuration can be seen, wherein the section extends through the longitudinal axis of the auxiliary module 2.

As mentioned, the receiving unit 40 is mounted in the housing 20 in such a manner that it can be displaced in the axial direction. As can be seen in FIG. 3, in the release configuration, the receiving unit 40 is on a distal end of its adjustment path. The receiving unit 40 is pretensioned into this position by the compression spring 80. Thus, when the receiving unit 40 is to be moved in the proximal direction relative to the housing 20, it must be moved against the pretensioning force of the compression spring 80. The receiving unit 40 can be displaced in the proximal direction relative to the housing 20 until a proximal end of the receiving unit 40 abuts against the proximal end wall of the housing 20.

In addition, in FIG. 3 it can be seen that the two retaining arms 43.1, 43.2 protrude outward from the body of the receiving unit 40, in that the protrusions 44.1, 44.2 of the retaining arms 43.1, 43.2 are received in the respective openings 31.1, 31.2 in the housing insert 30 and force guided in said openings. Since the retaining arms 43.1, 43.2 as a result point outward, the projections 45.1, 45.2, on the respective underside of the retaining arms 43.1, 43.2, do not extend into the internal space of the receiving unit 40 but are substantially flush with the inner surface of the receiving unit 40. In this position, the retaining arms 43.1, 43.2 are located in a release position.

Figure 4:
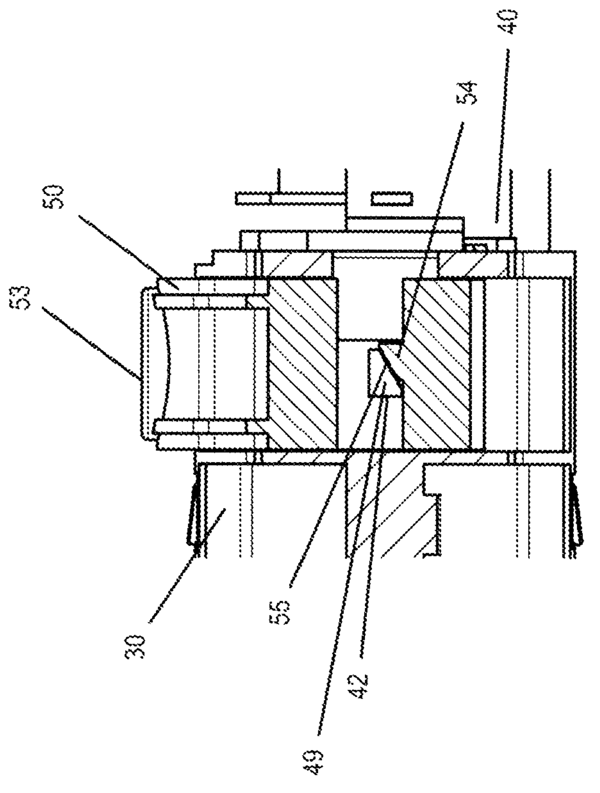

As mentioned above, the receiving unit 40 comprises on two outer faces a respective locking cam 42. The release button 50, on its inner face, comprises two mutually facing guiding cams 54, as can be seen in FIG. 4. FIG. 4 shows a middle region of the auxiliary module 2 in the release configuration, wherein the outer wall of the housing 20 and of the housing insert 30 and a limb of the U shape of the release button 50 are cut out in the representation, so that one of the guiding cams 54 and one of the locking cams 42 can be seen.

In the release configuration, the locking cams 42 are located on the distal side of the guiding cams 54. The locking cams 42 comprise a respective contact surface 49 which forms an acute angle with the longitudinal axis of the housing 20. The guiding cams 54 comprise a respective guiding surface 55 also oriented at this angle with respect to the longitudinal axis. In the release configuration, in which the receiving unit 40 is located on a distal end of its adjustment path, the guiding cams 54 are in a released position, in which the contact surfaces 49 of the locking cams 42 and the guiding surfaces 55 of the guiding cams 54 are located on top of one another. The guiding surface 55 is pretensioned radially outward, since the release button 50 is pretensioned by the release button spring 51.

Figure 5:
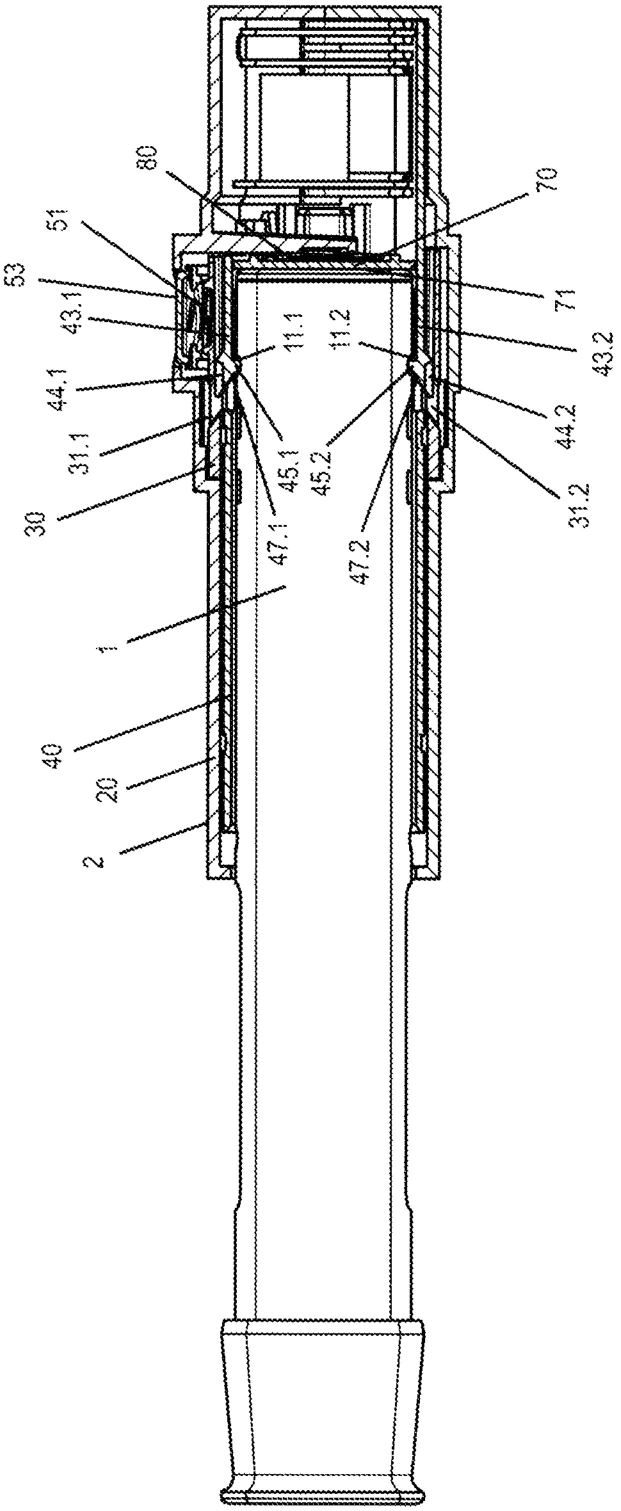

Adjustment from the Release Configuration into the Retaining Configuration (FIG. 5, 6)

For the connection of the injector 1 to the auxiliary module 2, the auxiliary module 2 must be adjusted from the release configuration into a retaining configuration. For this purpose, the receiving unit 40 must be displaced relative to the housing 20 from a distal end position into a proximal end position, as seen in FIG. 5.

This displacement occurs by means of the injector 1, in that said injector is inserted with its proximal end into the opening on the distal end of the housing 20 and moved in direction of the proximal end of the housing 20. Here, the inserted end of the injector 1 abuts against the abutment surface 71 of the abutment element 70. If the injector 1 is inserted further in the proximal direction into the housing 20, the abutment element 70 and the receiving unit 40 connected to the abutment element 70 are displaced against the pretensioning force of the compression spring 80 in the proximal direction, whereby the compression spring 80 is compressed. During this displacement, the retaining arms 43.1, 43.2 also move in the proximal direction, whereby the protrusions 44.1, 44.2 of the retaining arms 43.1, 43.2 slide out of the respective slanted openings 31.1, 31.2 in the housing insert 30 and as a result move toward the internal space of the housing 20 or the inserted injector 1. As a result, in each case, the protrusions 45.1, 45.2 on the undersides of the retaining arms 43.1, 43.2 also move toward the injector 1 and engage with increasing displacement of the receiving unit 40 in the proximal direction in recesses 11.1, 11.2 or grooves in the injector 1. See FIG. 5.

During this movement of the retaining arms 43.1, 43.2, the proximal sliding surfaces 46.1, 46.2 of the protrusions 44.1, 44.2 slide along an inner surface of the respective openings 31.1, 31.2 until they have reached the end of the opening 31.1, 31.2. The protrusions 44.1, 44.2 at that moment slide out of the opening 31.1, 31.2 and are forced inward toward the internal space with an additional displacement of the retaining arms 43.1, 43.2 in the proximal direction through an inner wall of the housing insert 30. Thereby, the projections 45.1, 45.2 are pressed farther toward the inserted injector 1 and engage in the recesses 11.1, 11.2 in the injector 1. During a further proximal displacement of the receiving unit 40, the protrusions 44.1, 44.2 are pulled further into the housing insert 30. This means that the protrusions 44.1, 44.2 are guided by the inner wall of the housing insert 30, so that the retaining arms 43.1, 43.2 can no longer pivot outward in the radial direction. The retaining arms 43.1, 43.2 are thus locked by the housing insert 30, and the projections 45.1, 45.2 cannot accidentally be released from the recesses 11.1, 11.2 in the injector 1. The retaining arms 43.1, 43.2 are now in a retaining position.

On its outer face, the injector can comprise a label or sticker, by means of which the recesses 11.1, 11.2 are covered. In this case, the label or the sticker can have H-shaped cuts above the recess 11.1, 11.2, in order to facilitate the engagement of the projections 45.1, 45.2 into the recesses 11.1, 11.2.

During the displacement of the receiving unit 40 from the distal end position into the proximal end position, the locking cams 42 of the receiving unit 40 also interact with the guiding cams 54 of the release button. In fact, as soon as the receiving unit 40 is displaced from its distal end position in the proximal direction, the slanted contact surfaces 49 of the locking cams 42 of the receiving unit 40 press against the respective slanted guiding surfaces 55 of the guiding cams 54 of the release button 50. Since the release button 50 cannot move in the axial direction but is mounted in such a manner that it can be moved in the radial direction, the guiding cams 54 are displaced by the pressure from the locking cams 42 against the pretensioning force of the release button spring 51 in the radial direction. As a result, the release button 50 is moved toward the housing 20 interior. In other words, the pressure from the locking cams 42 onto the guiding surfaces 55 set at an angle generates a movement of the guiding cams 54 and thus of the release button 50 in a radial direction perpendicular to the displacement direction of the receiving unit 40. This movement of the release button 50 has to occur against the spring force of the release button spring 51, and the release button spring 51 is correspondingly compressed. By the additional insertion of the injector 1 and as a result further displacement of the receiving unit 40 in the proximal direction, the slanted contact surfaces 49 of the locking cams 42 slide along the guiding surfaces 55 and thus further push the release button 50 radially toward the housing 20 until the locking cams 42 slide out over the guiding surfaces 55, as a result releasing the guiding cams 54. At that moment the release button 50 springs again radially outward away from the housing 20 due to the spring force of the release button spring 51. The locking cams 42 are then located on the proximal side of the guiding cams 54. In this position, the guiding cams 54 are located in their retaining position, in which they prevent the locking cams 42 from moving in the distal direction by means of a locking surface 56 oriented perpendicular to the longitudinal axis. In this position, the receiving unit 40 is located on a proximal end of its adjustment path, and the auxiliary module 2 is located in the retaining configuration.

This adjustment of the guiding cams 54 from their released position into their retaining position occurs simultaneously with the adjustment of the retaining arms 43.1, 43.2 from their release position into their retaining position during the adjustment movement of the receiving unit 40 from the distal end of the adjustment path toward the proximal end of the adjustment path of the receiving unit 40.

Retaining Configuration of the Auxiliary Module

FIG. 5 shows the auxiliary module 2 in a cross-sectional view in the retaining configuration with an injector 1 retained in the housing 20. Said injector contacts with its front surface the abutment surface 71 of the abutment element 70, wherein the abutment element 70 within the receiving unit 40 is located on the proximal end of the adjustment path of the abutment unit 40. The compression spring 80 is fully compressed in this position of the receiving unit 40. By the above-described interaction of locking cams 42 and guiding cams 54, the receiving unit 40 is retained therein by the position which is pretensioned by the compression spring 80. The retaining arms 43.1, 43.2 are located in their retaining position, in which the respective projections 45.1, 45.2 engage in the recesses 11.1, 11.2 in the injector 1, and in which the inner wall of the protrusions 44.1, 44.2 locks the retaining arms 43.1, 43.2. Thus, the injector 1 is immovably retained in the retaining configuration in the housing 20.

Figure 6:
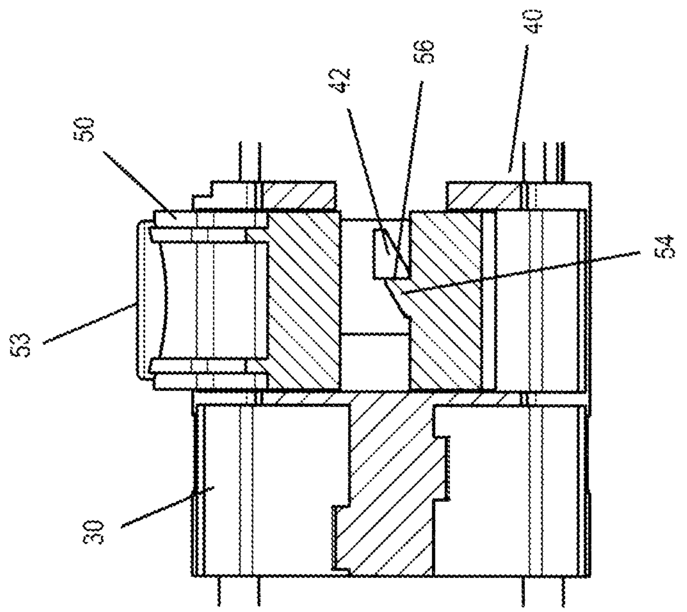

FIG. 6 shows a middle section of the auxiliary module in the retaining configuration. Here, as in FIG. 4, an outer wall of the housing 20 and of the housing insert 30 as well as a portion of the limb of the release button 50 are cut away, so that one of the guiding cams 54 of the release button 50 and one of the locking cams 42 of the receiving unit 40 can be seen. In FIG. 6, the guiding cam 54 is shown in its retaining position. In this retaining position, the guiding cam 54 with its locking surface 56 and by means of the pretensioning force of the release button 50 generated with the release button spring 51 prevents the locking cam 42 and thus the receiving unit 40 from moving in a distal direction. Thus, an undesired displacement of the receiving unit 40 is not possible, and the injector 1 cannot be accidentally released from the housing 20 of the auxiliary module 2. Since, in the retaining configuration, the receiving unit 40 is located entirely on the proximal end of its adjustment path, it can also not be displaced further in the proximal direction.

Adjustment from the Retaining Configuration into the Release Configuration

In order to separate the injector 1 from the auxiliary module 2, the auxiliary module 2 must be adjusted from the retaining configuration into the release configuration. This is achieved in that the actuation surface 53 of the release button 50 is pressed, so that the release button is displaced along its securing path in the radial direction toward the housing 20. Thereby, the release button spring 51 is compressed, and the guiding cams 54 are displaced from their retaining position into a release position, whereby the locking cams 42 of the receiving unit 40 can be released and moved in the distal direction.

Thereby, the compression spring 80 compressed in the retaining configuration can relax and as a result it presses against the abutment element 70, resulting in the abutment element 70 and the receiving unit 40 being displaced in the distal direction.

Here, the actuation surface 53 only needs to be pressed briefly, since, due to the pretensioning force of the compression spring 80, the receiving unit 40 moves immediately in the distal direction, so that the locking cams 42 are displaced toward the distal side of the guiding cams 54. If the actuation surface 53 is released, due to the spring force of the release button spring 51, the release button 50 is displaced again radially outward, whereby the guiding cams 54 are displaced upward into their released position.

Due to this displacement of the receiving unit 40 in the distal direction, the retaining arms 43.1, 43.2 are also displaced in the distal direction. The protrusions 44.1, 44.2 here extend along the inner wall of the housing insert 30 until the protrusions 44.1, 44.2 are located above the inlet of the respective openings 31.1, 31.2. During the further displacement of the receiving unit 40 in the distal direction, the protrusions 44.1, 44.2, due to their shape, are introduced into the openings 31.1, 31.2 and force guided in the openings 31.1, 31.2. The distal sliding surfaces 47.1, 47.2 of the protrusions 44.1, 44.2 then slide along the inner surface of the respective opening 31.1, 31.2, whereby the retaining arms 43.1, 43.2 are moved outward at a slant away from the internal space of the receiving unit 40. Thereby, the projections 45.1, 45.2 are also moved away from the internal space or from the injector 1, whereby the injector 1 is released from the retaining arms 43.1, 43.2.

Due to the force of the compression spring 80, the receiving unit 40 is displaced to the distal end of its adjustment path, wherein it abuts against a distal abutment on the housing 20. During this movement of the receiving unit 40, the free ends of the retaining arms 43.1, 43.2 are inserted further into the respective openings 31.1, 31.2 in the housing insert 30 until the retaining arms 43.1, 43.2 are in their release position. During the entire displacement of the receiving unit 40, the abutment surface 71 displaces the injector 1 with the receiving unit 40 in the distal direction, so that the injector can simply be removed from the housing. When the receiving unit 40 has arrived on the distal end of its adjustment path, the auxiliary module is in the release configuration and the injector 1 can be removed from the housing 20.

Anti-Twist Device

Figure 7:
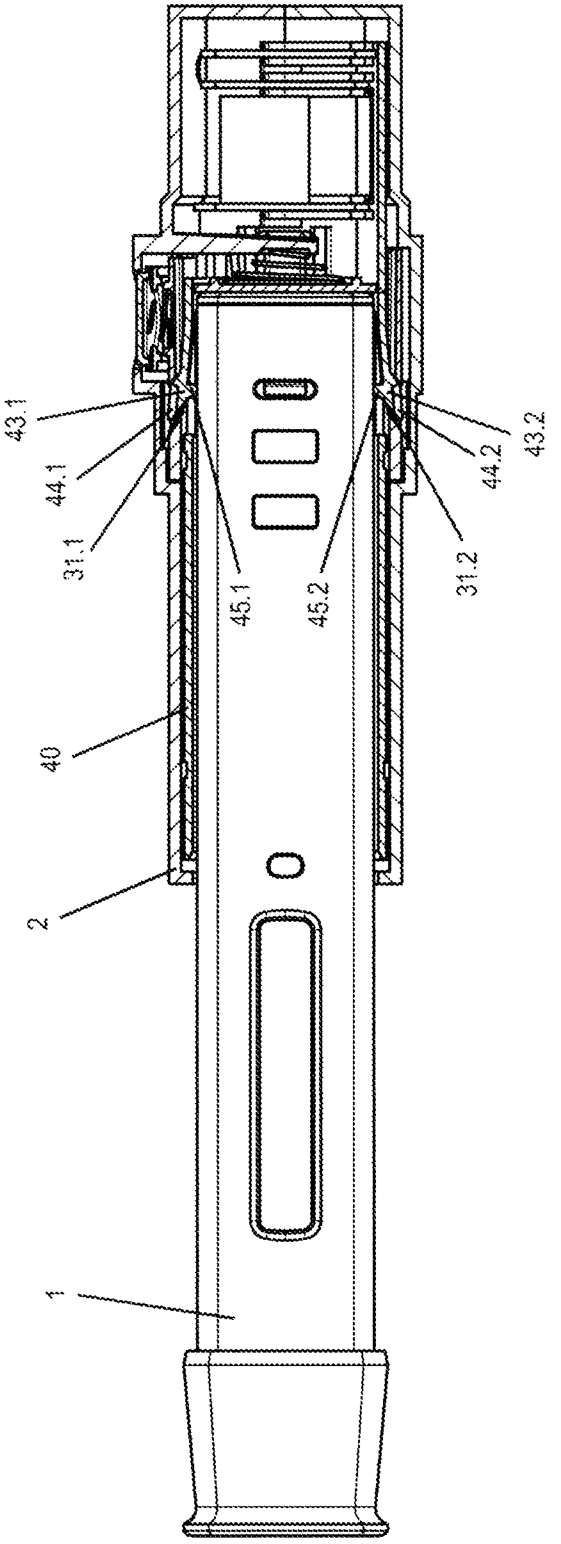

In FIG. 7, the auxiliary module 2 can be seen in a cross-sectional view with inserted injector 1. However, in contrast to the representation shown in FIG. 5, the injector 1 is not inserted correctly. In fact, the injector 1 shown comprises recesses 11.1, 11.2 on only two sides, into which the projections 45.1, 45.2 of the retaining arms 43.1, 43.2 can engage. However, in the position of the injector shown in FIG. 7, these recesses 11.1, 11.2 are not aligned with the projections 45.1, 45.2. As can be seen in FIG. 7, although the injector 1 can be introduced into the housing, the receiving unit 40 cannot be moved completely into the proximal end position.

Since the projections 45.1, 45.2 do not engage in the recesses 11.1, 11.2 in the injector 1 but are set on an outer surface of the injector 1, the retaining arms 43.1, 43.2 cannot be moved into their retaining position and remain pivoted outward. As a result, the protrusions 44.1, 44.2 of the retaining arms 43.1, 43.2 cannot be moved completely out of the openings 31.1, 31.2. As a result, the protrusions 44.1, 44.2 lock the receiving unit 40, so that the receiving unit can no longer be displaced in the proximal direction. Thus, the locking cam 42 cannot move the guiding cam 54 out of its released position. This means that, in the position of the injector 1 shown in FIG. 7, the auxiliary module 2 cannot be transferred into its retaining configuration, and the injector 1 can thus not be retained in the housing 20.

Alternative Embodiments

Figure 9:
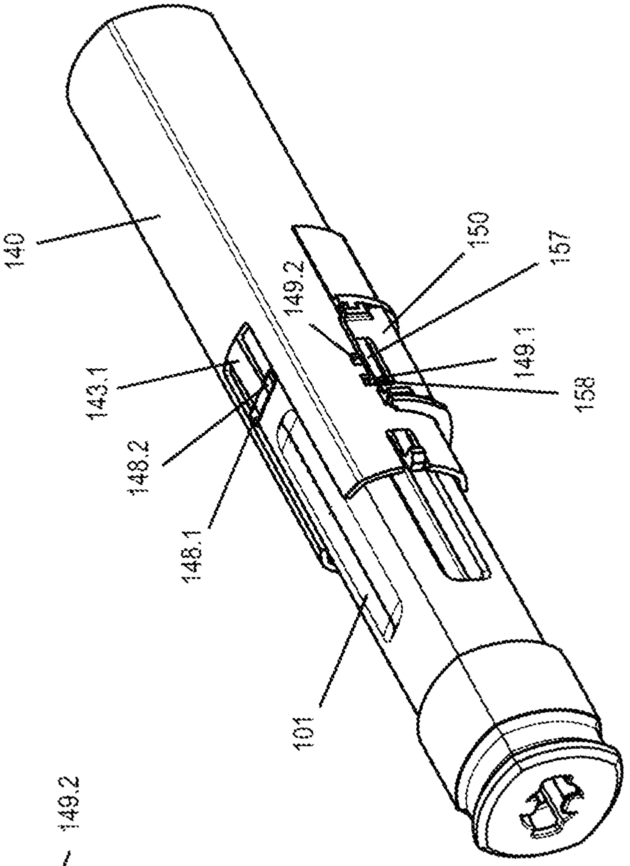
Figure 8:
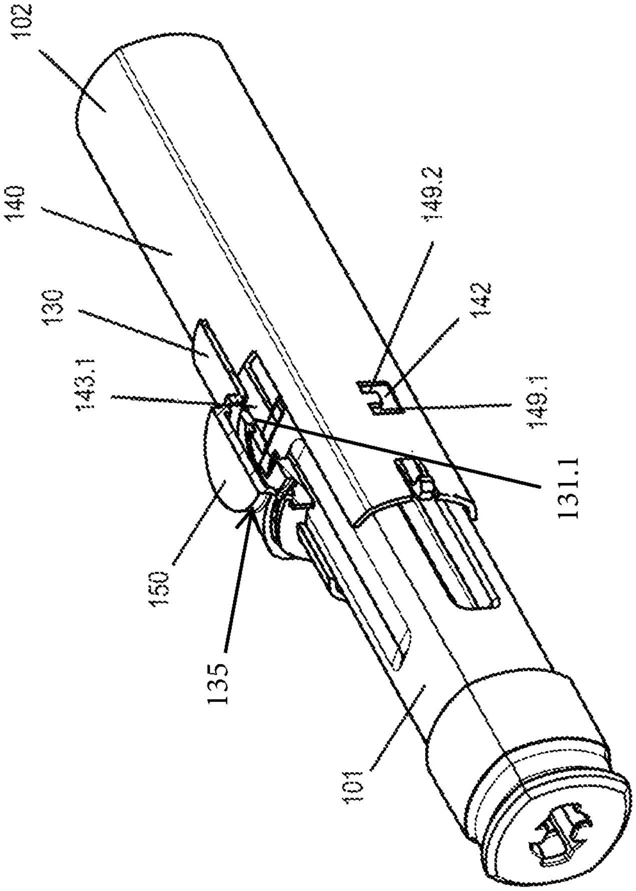

In FIGS. 8 and 9, an additional embodiment of the auxiliary module 102 according to the invention, which is connected to an injector 101, is represented.

FIGS. 8 and 9 each show the auxiliary module 102 in the retaining configuration. In the representation in FIG. 8, on the side, half of the release button 150 and of the housing insert 130 is cut out of the representation, so that the retaining arm 143.1 can be seen better. In addition, in order to simplify the representation, the release button spring is not represented. In FIG. 9, the upper half of the release button 150 and of the housing insert 130 has been removed from the representation.

In contrast to the embodiment described in FIGS. 1-7, in the auxiliary module 102 according to FIGS. 8 and 9, the retaining arms 143, the release button 150 and the retaining device or retainer are arranged in a proximal region of the auxiliary module 102. Accordingly, the retaining arms 143.1 do not interact as in the embodiment according to FIGS. 1-7 with distal recesses in the injector 101, but with recesses which, when viewed in the longitudinal direction, are arranged in a middle region of the injector 101. In addition, the retaining arms 143.1 of the auxiliary module 102 (more specifically the receiving unit 140) according to FIGS. 8 and 9 are shaped differently. Furthermore, the retaining device or retainer 135 is also designed differently.

As in the embodiment in FIGS. 1-7, the first of the two retaining arms 143.1 is arranged on a first side and the second retaining arm is arranged on one of the sides of the substantially square shape of the receiving unit 140, which faces the first side. However, the retaining arms 143.1 have no protrusions which are arranged in the radial direction on the retaining arms, but instead they have guide pins 148.1, 148.2 arranged in a direction transverse to the longitudinal axis of the auxiliary module 102 to the side or at the sides of the respective retaining arms, e.g., 143.1. In addition, as described in the first embodiment, on an inner face facing the internal space of the receiving unit 140, the retaining arms 143.1 comprise a respective projection (not visible in FIGS. 8 and 9). These projections engage in the retaining configuration into respective recesses in the injector 101, analogously to prior-described embodiments.

The receiving unit 140, on two respective facing sides, comprises a U-shaped recess 142 with a first limb (or leg) 149.1 and a second limb (or leg) 149.2. The release button 150 has two mutually facing clip-on arms 157 (visible in FIG. 9 at only one facing side of receiving unit 140) oriented in the direction of the longitudinal axis of the receiving unit 140, which comprise a cam 158 on their respective free ends. In the retaining configuration, said cam 158 engages in the first limb 149.1 of the U-shaped recess 142, whereby the receiving unit 140 is locked and cannot be moved in the distal direction.

In order to switch from the retaining configuration into the release configuration, the release button 150 is pressed in the radial direction towards the housing insert 130, whereby the clip-on arms 157 are moved relative to the housing insert 130, so that they are moved downward out of the limb 149.1 of the U-shaped recess 142. Thereby, the receiving unit 140 is released and can be displaced in the distal direction, whereby the injector 101 is released from the receiving unit 140.

During the release of the release button 150, said release button moves again radially outward. Thereby, the cams 158 of the clip-on arms 157 are introduced into the second limb 149.2 of the U-shaped recess 142.

In a distal displacement of the receiving unit 140 relative to the housing insert 130, the receiving pins 148.1, 148.2 of the retaining arms, e.g., 143.1, are introduced into lateral openings 131.1 in the housing insert 130, analogously to the guiding of the retaining arms in the first described embodiment according to FIGS. 1-7. Due to this movement, the retaining arms 143.1 in the openings 131.1 are moved outward at a slant, away from the internal space of the receiving unit 140. Thereby, the injector 101 is released from the projections of the retaining arms, e.g., 143.1.

During the adjustment of the auxiliary module 102 from the release configuration into the retaining configuration, the receiving unit 140 is displaced in the proximal direction relative to the housing insert 130. Here, the cams 158 of the clip-on arms 157 are displaced from the first limb 149.1 of the U-shaped recess 142 to the second limb 149.2. To enable this, the respective distal side walls of the limbs 149.1, 149.2 comprise a beveling on which the cams 158 can slide out of the limbs 149.1, 149.2.

In an additional embodiment, the clip-on arms can also be arranged rotated by 180°, from their orientation as shown in the embodiment in FIGS. 8 and 9. In this case, the free end of the clip-on arms faces the proximal end of the housing 20. Accordingly, in this embodiment, the proximal side walls of the limbs comprise a beveling for the cams of the clip-on arms.

Figure 11:
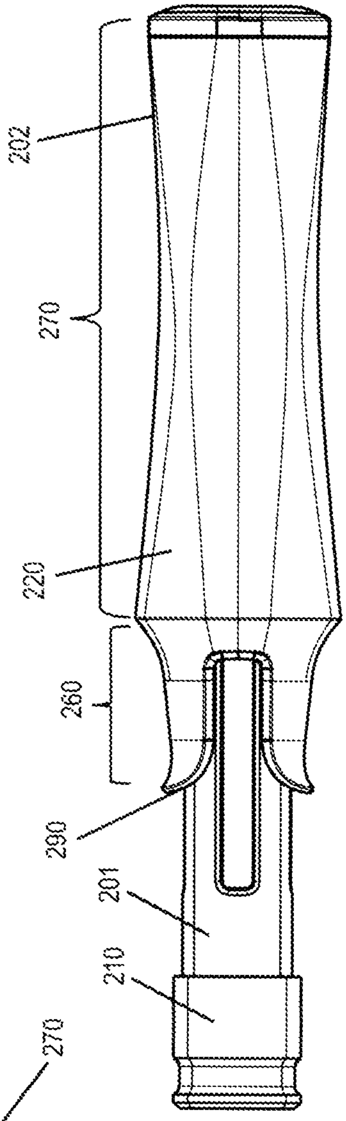
Figure 12:
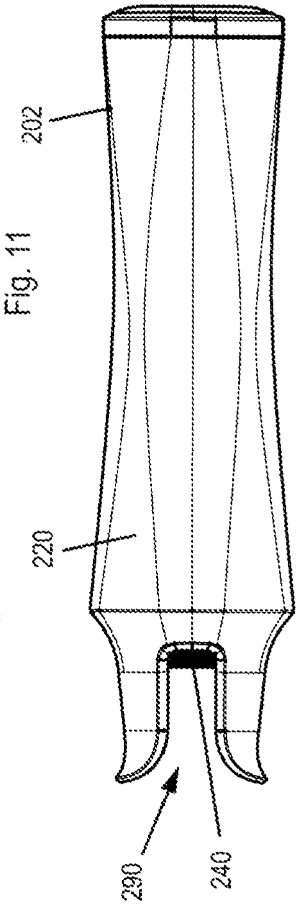
Figure 10:
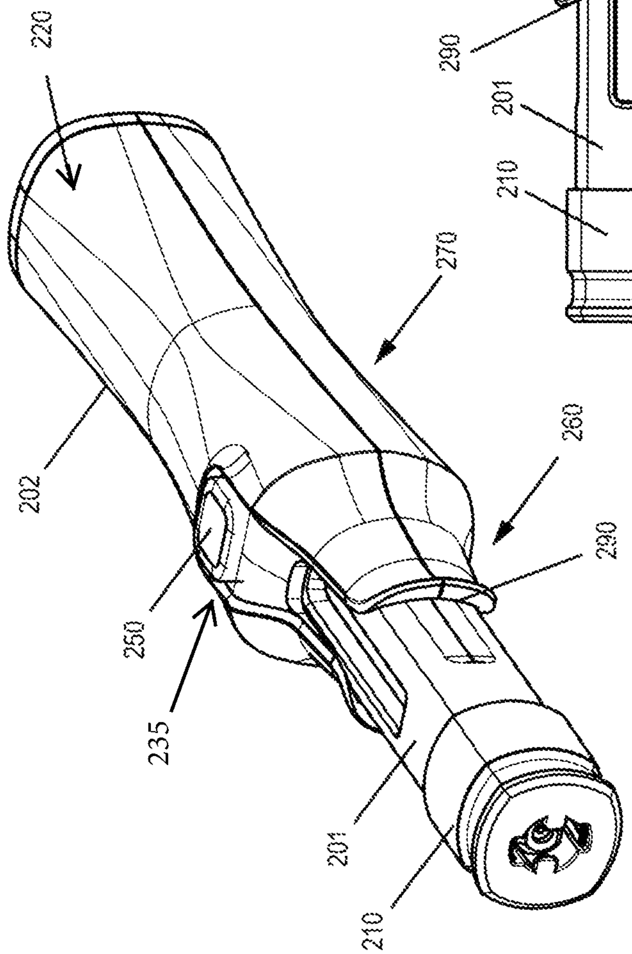

In FIGS. 10-12, an additional embodiment of the auxiliary module 202 according to the invention is shown. FIG. 10 shows a perspective view from the front, while FIG. 11 shows a side view of the auxiliary module 202. FIG. 12 represents a side view of the auxiliary module 202 without inserted injector 201.

In comparison to the above-described embodiments, the embodiment shown in these figures has a differently shaped outer contour. Thus, in FIGS. 10-12, it can be seen that the housing 220 of the auxiliary module 202 comprises a distal section 260 and a proximal section 270. The periphery of the distal section 260 increases toward the proximal section 270, whereby a beveling is formed.

In comparison to the distal section 260, the proximal section 270 is substantially longer and has a concave shape. This concave shape forms a handle surface by which the user can hold the auxiliary module 202. The distal section 260 can also be used as a handle, in particular when the user, before use, must pull off a needle protection cap 210 from the injector 201 in the axial direction. While the user grasps the auxiliary module 202 with one or more fingers on the distal section 260, the beveling of the distal section 260 serves as an axial support for the hand, so that the needle protection cap 210 can be removed without problem from the injector 201.

With reference to FIGS. 10-12, the retaining device or retainer 235 with the release button 250 and the retaining arms are arranged, as in the embodiment according to FIGS.

8 and 9, in a distal region of the housing 220. In contrast to the above-described embodiments according to FIGS. 1-9, the opening 290 in the housing 220 into which the injector 201 is introduced is designed in the shape of a funnel, whereby the injector 201 can be introduced more simply. The funnel-shaped opening 290 is interrupted in its peripheral direction so that the inspection window of the injector 201 is not covered by the housing 220 of the auxiliary module 202.

When the injector 201 is not connected to the auxiliary module 202, as shown in FIG. 12, the receiving unit protrudes slightly beyond a distal end edge of the housing 220, so that a small region 240 of the receiving unit can be seen from outside. This region 240 of the receiving unit may be marked in red, so that it can easily be seen by the user. If the injector 201 is inserted into the opening 290 with successful entry of the retaining configuration and as a result the receiving unit is displaced relative to the housing 220, as described above, the region 240 of the receiving unit moves distally into and disappears in the housing 220. If the auxiliary module 202 is properly in its retaining configuration, the region 240 marked in red of the receiving unit can no longer be seen from outside. As a result, it is indicated to the user that the injector 201 is correctly connected to the auxiliary module 202. On the other hand, if the retaining arms do not engage correctly into the injector 201 and the retaining arms are not locked by the housing insert, at least a portion of the region 240 marked in red remains visible from outside. This indicates that the injector 201 is not correctly connected to the auxiliary module 202 and consequently the auxiliary module 202 is not in the retaining configuration.

The invention is not limited to the above-described embodiment examples. Thus, for example, in an alternative to the embodiments according to FIGS. 1-12, the released position of the guiding cam can be located in a lower region in the vicinity of the release position. This means that, after its actuation, the release button remains in a pressed position and that it is moved radially outward only after an injector has been correctly inserted and the auxiliary module is in the retaining configuration.

The locking of the receiving unit on the housing can also be implemented differently than with a guiding cam and a locking cam. For example, the receiving unit can be secured by means of a threaded connection on the housing. The adjustment from the retaining configuration into the release configuration does not necessarily have to occur with a release button. Instead, in a variant, the auxiliary module can also be adjusted by manual displacement of the receiving unit.

In addition, the embodiment of the invention can also deviate in other ways from the described embodiment examples. Thus, for example, the auxiliary module can also comprise only one retaining arm and/or only one guiding cam or only one locking cam.

Furthermore, for example, the auxiliary module can also be used for an injector other than an autoinjector. The housing of the auxiliary module can have a different shape than the shape shown in FIGS. 1 to 12. In particular, the housing does not have to surround the injector completely but can instead receive, for example, the injector only over a section or only over a partial circumference. In addition, the receiving unit can also be designed to have a different shape than that of a sleeve. For example, it can be designed to be much shorter, in the form of a ring or a bracket or clamp on which the retaining elements are arranged.

Moreover, the compression spring between the abutment element and the housing wall of the housing is not absolutely necessary. The mechanism according to the invention also works without a compression spring. In this case, the receiving unit can be adjusted, i.e., axially moved, manually. Furthermore, a housing insert is not absolutely necessary. The guiding path or opening of the retaining arms can also be formed directly in the housing or in another element.

LIST OF REFERENCE NUMERALS

1, 101, 201 Injector
2, 102, 202 Auxiliary module
11.1, 11.2 Recesses
20, 220 Housing
21 Upper housing half
22 Lower housing half
23 Opening
30, 130 Housing insert
31.1, 31.2 Opening
32.1, 32.2 Support surfaces
33 Aperture
34 Ribs
35, 135, 235 Retaining device or retainer
40, 140 Receiving unit
41 Section
42 Locking cam
43.1, 43.2, 143.1 Retaining element
44.1, 44.2 Protrusion
45.1, 45.2 Projection
46.1, 46.2 Proximal sliding surface
47.1, 47.2 Distal sliding surface
49 Contact surface
50, 150, 250 Release button
51 Release button spring
53 Actuation surface
54 Guide cam
55 Guide surface
56 Locking surface
60 Electronics module
70 Abutment element
71 Abutment surface
80 Compression spring
142 U-shaped recess
148.1, 148.2 Guide pins
149.1, 149.2 Limb or leg
157 Clip-on arm
158 Cam
210 Needle protection cap
240 Region receiving unit
260 Distal section
270 Proximal section
290 Opening

The invention claimed is:

1. An auxiliary module for connecting to an injector for dispensing a medical substance, the auxiliary module comprising:

a housing with a longitudinal axis extending between a proximal end and a distal end of the housing, the housing defining a housing interior with a closed proximal end and an open distal end;

a retainer comprising a sleeve-shaped insert arranged within the housing interior; and a receiving unit with a retaining element, wherein the receiving unit is sleeve-shaped, a half shell or a plate with a circumferential wall forming a cavity configured for accommodating the injector, and the receiving unit is movable linearly along the longitudinal axis relative to the housing, wherein:

a. the auxiliary module has a retaining configuration, in which the receiving unit is retained in the housing by the retainer and in which the retaining element forms an engagement with the injector such that the injector is retained by the receiving unit; and b. the auxiliary module has a release configuration, in which the receiving unit is released from the retainer and the injector is released from the engagement with the retaining element, wherein the auxiliary module is adjustable from the retaining configuration into the release configuration, and back again, by an adjustment movement of the receiving unit along the longitudinal axis, and wherein the insert comprises ribs engaged in grooves of the housing interior such that the insert is non-movable relative to the housing during the adjustment movement.

2. The auxiliary module according to claim 1, wherein, in the retaining configuration, the retaining element is locked by the insert.

3. The auxiliary module according to claim 1, wherein the housing is sleeve-shaped and, in the retaining configuration, at least partially surrounds the injector when the injector is introduced into the housing.

4. The auxiliary module according to claim 1, wherein the receiving unit is pretensioned by an elastic element in a direction of the longitudinal axis of the housing in the retaining configuration.

5. The auxiliary module according to claim 1, wherein the retaining element for retaining the injector is movable substantially in a direction perpendicular to the longitudinal axis of the housing and the retaining element comprises a projection for cooperating with the injector.

6. The auxiliary module according to claim 5, wherein in an area of a free end of the retaining element, the retaining element comprises a protrusion for engaging in the housing upon a forced release of the projection from the injector.

7. The auxiliary module according to claim 6, wherein, in the retaining configuration, the retaining element is in a retaining position, in which the protrusion is locked by the housing, so that the retaining element cannot be moved relative to the receiving unit and in which the projection engages in the injector when the injector is inserted in the housing.

8. The auxiliary module according to claim 7, wherein the auxiliary module is adjustable into the retaining configuration only when the retaining element is moved into the retaining position of the retaining element.

9. The auxiliary module according to claim 6 wherein, in the release configuration, the retaining element is in a release position, in which the protrusion is received in a recess in the housing and in which the projection is pulled back from an internal space of the receiving unit, so that the injector is released from the projection.

10. The auxiliary module according to claim 1, wherein the retainer comprises a guiding cam and the receiving unit comprises a locking cam, wherein, in the retaining configuration, the guiding cam cooperates with the locking cam such that the receiving unit is immovably retained in the housing.

11. The auxiliary module according to claim 10, wherein the guiding cam is displaced along a securing path and adjusted from a retaining position, in which the guiding cam cooperates with the locking cam, into a release position, in which the locking cam is released from the guiding cam, and wherein the guiding cam is pretensionable by an elastic securing element into the retaining position of the guiding cam.

12. The auxiliary module according claim 1, wherein the retainer comprises a release button coupled to the insert, the release button comprising an actuation surface protruding through the housing to an exterior thereof, the actuation surface configured to be manually actuated by a user by means of which the auxiliary module can be adjusted from the retaining configuration into the release configuration.

13. The auxiliary module according to claim 1, wherein the retaining element comprises at least one projection configured to be received in an at least one recess of the injector when the retaining element and the at least one recess are rotationally aligned around a longitudinal axis of the auxiliary module, and travel of the at least one projection initiated by a movement of the receiving unit in a direction to be received in the at least one recess is prevented when the at least one projection of the retaining element is not properly rotationally aligned, such that only in a certain rotational orientation in the housing can the receiving unit be moved completely into a proximal end position in the auxiliary module, and resultingly, the auxiliary module cannot be transferred into the retaining configuration with the injector and the injector also cannot be retained in the housing.

14. The auxiliary module according to claim 13, wherein the at least one projection of the retaining element comprises a first projection and a second projection, and wherein the at least one recess comprises a recess on each of two sides of the injector, into which the first projection and the second projection can be received and the auxiliary module cannot be transferred into the retaining configuration with the injector unless the recess on each of the two sides are rotationally aligned with the first projection and the second projection.

15. The auxiliary module according claim 1, wherein the retainer comprises a release button, with a U-shaped cross section, mounted on the insert, so that legs of the U-shaped cross section surround the insert.

16. The auxiliary module according claim 15, wherein the release button is movable radially, in a direction perpendicular to the longitudinal axis of the housing, relative to the insert and to the housing along a linear securing path.

17. The auxiliary module according claim 1, wherein in the retaining configuration, the retaining element comprises holding arms engaged with recesses of the injector in the engagement between the retaining element and the injector.

* * * * *